US00PP23269P2

(12) United States Plant Patent
Bédard

(10) Patent No.: US PP23,269 P2
(45) Date of Patent: Dec. 25, 2012

(54) FLORIBUNDA ROSE PLANT NAMED 'WEKBIJOU'

(50) Latin Name: *Rosa hybrida*
Varietal Denomination: WEKbijou

(75) Inventor: Christian Bédard, Brea, CA (US)

(73) Assignee: Weeks Roses, Pomona, CA (US)

( * ) Notice: Subject to any disclaimer, the term of this patent is extended or adjusted under 35 U.S.C. 154(b) by 0 days.

(21) Appl. No.: 13/373,157

(22) Filed: Nov. 7, 2011

(51) Int. Cl.
*A01H 5/00* (2006.01)

(52) U.S. Cl. ..... Plt./141

(58) Field of Classification Search ..... Plt./141
See application file for complete search history.

*Primary Examiner* — June Hwu
*Assistant Examiner* — Louanne Krawczewicz Myers
(74) *Attorney, Agent, or Firm* — McKee, Voorhees & Sease, P.L.C.

(57) ABSTRACT

A new variety of Floribunda rose suitable for garden decoration, having flowers of milk chocolate changing to lavender coloration.

1 Drawing Sheet

Classification: The present invention relates to a new *Rosa hybrida* plant.

Variety denomination: The new plant has the varietal denomination 'WEKbijou'.

BACKGROUND OF THE INVENTION

This invention relates to a new and distinct variety of Floribunda Rose. It has as its seed parent the variety known as 'WEKcryplag' (U.S. Plant Pat. No. 10,072) and as its pollen parent the variety known as 'DICdivine' (not patented).

SUMMARY OF THE INVENTION

Among the features which distinguish the new variety from other presently available and commercial rose cultivars known to the inventor are the following combinations of characteristics: its unusual milk chocolate changing to lavender flower coloration, its very abundant bloom, its variable to somewhat long length filaments (about 0.7 to about 1.6 cm.) and its moderately vigorous growth for this color range. The plant has a bushy rounded growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKbijou' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKcryplag' by the following combination of characteristics: whereas 'WEKbijou' bears very double flowers (about 30 to 49 petals) of milk chocolate changing to lavender coloration, 'WEKcryplag' bears semi-double flowers of clear lavender coloration with significantly lesser petalage (about 12 to 16 petals). The new variety has a bushy rounded medium height growing habit (about 105 to about 140 cm. in height), whereas the seed parent has a bushy upright significantly shorter growing habit (about 90 to about 100 cm. in height).

The new variety may be distinguished from its pollen parent, 'DICdivine' by the following combination of characteristics: whereas 'WEKbijou' bears very double flowers (about 30 to 49 petals) of milk chocolate changing to lavender coloration, 'DICdivine' bears double flowers of medium yellow coloration with significantly lesser petalage (about 32 petals). The new variety has a bushy rounded medium height growing habit (about 105 to about 140 cm. in height), whereas the pollen parent has an upright somewhat spreading significantly shorter growing habit (about 80 cm. in height).

COMPARISON WITH THE CLOSEST COMMERCIALLY AVAILABLE CULTIVAR

The new variety may be distinguished from its closest commercially available cultivar, 'WEKsproulses' (U.S. Plant Pat. No. 17,822) by the following combination of characteristics: whereas 'WEKbijou' bears very double flowers (about 30 to 49 petals) of milk chocolate changing to lavender coloration, 'WEKsproulses' bears double flowers of warm golden brown coloration with significantly lesser petalage (about 23 to 32 petals). The new variety bears medium size flower (about 8.6 to about 11.8 cm. in diameter), whereas the closest commercially available cultivar bears significantly larger flower (about 9.4 to about 14.3 cm. in diameter).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The following photograph illustrates a 3 to 4 year-old rose plant of the new variety grown outdoors in Wasco, Calif. in the month of November. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in regular rounded clusters on strong somewhat short to medium length stems (about 15 to about 62 cm.). Outdoors, the plant blooms very abundantly and nearly continuously during the growing season. The flowers have a moderate apple-like to spicy fragrance.

BUD

The peduncle is about 3.4 to about 6.3 cm. in length, of average caliper (about 0.3 to about 0.4 cm. in diameter), and usually erect. It is moderately smooth, with some stipitate glands and few hairs. Peduncle color is between 146B and 151A sometimes lightly suffused, especially on the side exposed to the sun, with between 187B and 183A.

Before the calyx breaks, the bud is about 1.3 to about 1.7 cm. in diameter at the widest point, about 1.8 to about 2.3 cm. in length, and moderately pointed to somewhat ovoid in shape with a conspicuous neck. The surface of the bud bears between 6 to 9 foliaceous appendages with few stipitate glands and hairs, usually with slender entire foliaceous parts extending beyond the tip of the bud about ¼ or more of its length. Bud color is between 146B and 151A.

The sepals are about 2.8 to about 4.1 cm. in length and about 0.7 to about 1.1 cm. in width at the widest point. The outer surface color of the sepal is between 146B and 151A. The outer surface texture of the sepal is smooth with few stipitate glands and hairs. The inner surface color of the sepal is near 146A broadly bordered by near 139A. After the sepals open, the inner surface color is often heavily suffused, especially on the area exposed to the sun, with between 187A and 187B. The inner surface of the sepal is covered with fine wooly tomentum; sepal margins are lined with some stipitate glands and hairs.

The receptacle of the flower is of medium length (about 0.5 to about 0.7 cm.) and moderately heavy in caliper (about 0.8 to about 1.1 cm. in diameter). The receptacle is urn-shaped in form. Its surface is smooth with some hairs and with moderately thick fleshy walls. The receptacle color is between 144A and 146B.

As the petals open (after the calyx breaks), the bud is about 1.8 to about 2.1 cm. in diameter at the widest point, about 2.3 to about 3.0 cm. in length, and ovoid to somewhat pointed in form. The color of the under surfaces of the newly opened petals is between 176B and 165D often heavily suffused with between 60A and 60B. At the point where the petal attaches, there is a moderately large zone of between 1C and 154C. The color of the upper surfaces of the newly opened petals is between 177C and 174B. At the point where the petal attaches, there is a somewhat large zone of between 2B and 3B.

BLOOM

When fully open, the bloom ranges from about 8.6 to about 11.8 cm. in diameter. Petalage is very double with about 30 to 49 petals and about 11 to 15 petaloids irregularly arranged. When partially open, the bloom form is ovoid to moderately high centered to somewhat cupped, and the petals are moderately tightly spiraled to cupped with petal edges somewhat reflexed outward. When fully open, the bloom form is cupped, and the petals are loosely cupped with petal edges moderately reflexed outward to somewhat rolled on the outermost petals.

PETALS

The substance of the petals is somewhat heavy and of moderately thin thickness, with upper surfaces moderately satiny and under surfaces somewhat shiny. The petals are about 2.2 to about 5.2 cm. in length and about 1.9 to about 4.7 cm. in width at the widest point. Petal margins are entire.

The outer petals are moderately obovate to somewhat rounded in shape with rounded apices.

The inner petals are oblanceolate to somewhat obovate in shape with rounded apices and sometimes slightly notched with one notch.

Petaloids are about 0.9 to about 3.5 cm. in length and about 0.3 to about 2.5 cm. in width at the widest point. Petaloids are irregularly shaped somewhat oblanceolate to obovate with rounded apices.

NEWLY OPENED FLOWER

The under surface color of the outer petals is between 36B and 36C often heavily suffused, especially on the outermost petals, with between 60B and 60A. At the point where the petal attaches, there is a moderately small zone of between 3B and 2B. The color at the base of the upper surface of the outer petals is between 161A and 161D gradually suffusing toward the middle of the petal with between 56C and 69C. At the point where the petal attaches, there is a large zone of between 6A and 7A.

The under surface color of the intermediate and inner petals is between 165D and 159B often lightly suffused with between 60B and 60A. The upper surface color of the intermediate and inner petals is between 161A and 161D.

The under and upper surface colors of the petaloids are similar in coloration to the upper and under surfaces of the intermediate and inner petals.

The general tonality of the newly opened flower is between 161A and 161D.

THREE-DAY-OLD FLOWER

The under surface color of the outer, intermediate and inner petals is between 75D and 76D often lightly suffused with between 60B and 60C. At the point where the petal attaches, there is a moderately small zone of near 2D. The upper surface color of the outer, intermediate and inner petals is between 69C and 76D sometimes lightly blushed toward the petal edge with between 60B and 72A. At the point where the petal attaches, there is a large zone of between 5C and 6C.

The under and upper surface colors of the petaloids are similar in coloration to the upper and under surfaces of the intermediate and inner petals.

The general tonality of the three-day-old flower is between 69C and 76D sometimes lightly blushed toward the petal edge with between 60B and 72A.

On the spent bloom, the petals usually drop off cleanly.

In November in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 225) and are arranged regularly about the pistils; some are mixed with petaloids. The filaments are of variable to somewhat long length (about 0.7 to about 1.6 cm.) most with anthers. Filaments are between 13B and 12A in color. The anthers are of medium size for the class and all open approximately at the same time. Anther color when immature is near 21B on the external part and near 10C on the internal part. Anther color at maturity is near 1658 on the external part and near 200A on the internal part. Pollen is abundant and between 16D and 18B in color.

FEMALE REPRODUCTIVE ORGANS

Pistils vary in number (average about 160). The styles are moderately even, somewhat short to average in length (about 0.4 to about 0.7 cm.), moderately thin in caliper and loosely separated. Stigma color is between 16C and 17D. Style color is between 8C and 10C often heavily suffused with between 53B and 53C. Ovaries are usually all enclosed in the calyx.

Hips have not been observed on this variety when grown in Wasco, Calif.

FOLIAGE

The compound leaves are usually comprised of three to seven leaflets and are borne abundantly. The seven-leaflet leaves are about 10.7 to about 14.7 cm. in length and about 6.9 to about 10.7 cm. in width at the widest point, moderately leathery to somewhat crisp in texture, and moderately glossy in finish on the upper side and matte in finish on the under side. The terminal leaflets are about 4.5 to about 6.3 cm. in length and about 2.2 to about 3.8 cm. in width at the widest point, shaped oval with acute apices and acute bases. Their margins are usually simply serrate. The venation pattern type is pinnate. The venation coloration of the upper surface is similar to the upper surface color of the mature leaf. The venation coloration of the lower surface is similar to the lower surface color of the mature leaf.

The upper surface color of the mature leaf is between 137A and 139A. The under surface color of the mature leaf is between 147B and 147C. The upper surface color of the young leaf is between 137A and 148B, often heavily suffused with between 187A and 183A. The under surface color of the young leaf is between 137D and 151A, often heavily suffused with between 187A and 183A.

The rachis is somewhat light in caliper and rough. The upper side is deeply grooved with some hairs and few stipitate glands on the edges of the grooves. The under side of the rachis is rough with very few stipitate glands and few small prickles. The rachis color is near 146D on the under side and near 146B on the upper side often moderately suffused on the young leaves with between 187A and 183A.

The stipules are about 1.4 to about 2.1 cm. in length and moderately wide (about 0.5 to about 0.8 cm.) with long straight points that usually turn out at an angle of more than 45 degrees. The under and upper surface color of the stipule is between 137A and 139A.

The petiole is somewhat light in caliper and rough. The upper side is deeply grooved with some hairs and few stipitate glands on the edges of the grooves. The under side of the petiole is rough with very few stipitate glands and few small prickles. The petiole is about 0.2 to about 0.9 cm. in length and about 0.1 to about 0.15 cm in width at the widest point. The petiole color is near 146D on the under side and near 146B on the upper side often moderately suffused on the young leaves with between 187A and 183A.

The plant displays an average degree of resistance to powdery mildew and rust as compared to other commercial varieties grown under comparable conditions in Wasco, Calif. The plant's winter hardiness and drought/heat tolerance are yet to be determined.

GROWTH

The plant has a bushy rounded medium height growing habit (about 105 to about 140 cm. in height and about 76 to about 92 cm. spread at the widest point), with full branching. It displays moderately vigorous growth and the canes are of somewhat light caliper for the class (about 1.1 to about 1.9 cm. in diameter at the widest point).

The color of the major stems is between 152A and 152B. They bear some large prickles that are about 0.5 to about 1.1 cm. in length. The large prickles are almost straight to angled slightly downward with a moderately short somewhat broad oval base; prickle color is near 165B. The major stem bears few small prickles of similar shape and coloration.

The color of the branches is between 146B and 146A. They bear some large prickles which are of similar size and shape to the large prickles on the major stems; prickle color is near 146D sometimes lightly suffused with near 53B. The branches bear few small prickles of similar shape and coloration.

The color of the new shoots is between 146C and 153A sometimes lightly suffused with between 187B and 183A. They bear some large prickles which are of similar shape to the large prickles on the major stems. The large prickles are about 0.4 to about 0.7 cm. in length. Prickle color is near 153C usually heavily suffused with near 187D. The shoots bear few small prickles of similar shape and coloration.

I claim:

1. A new and distinct Floribunda rose plant of the variety substantially as described and illustrated herein.

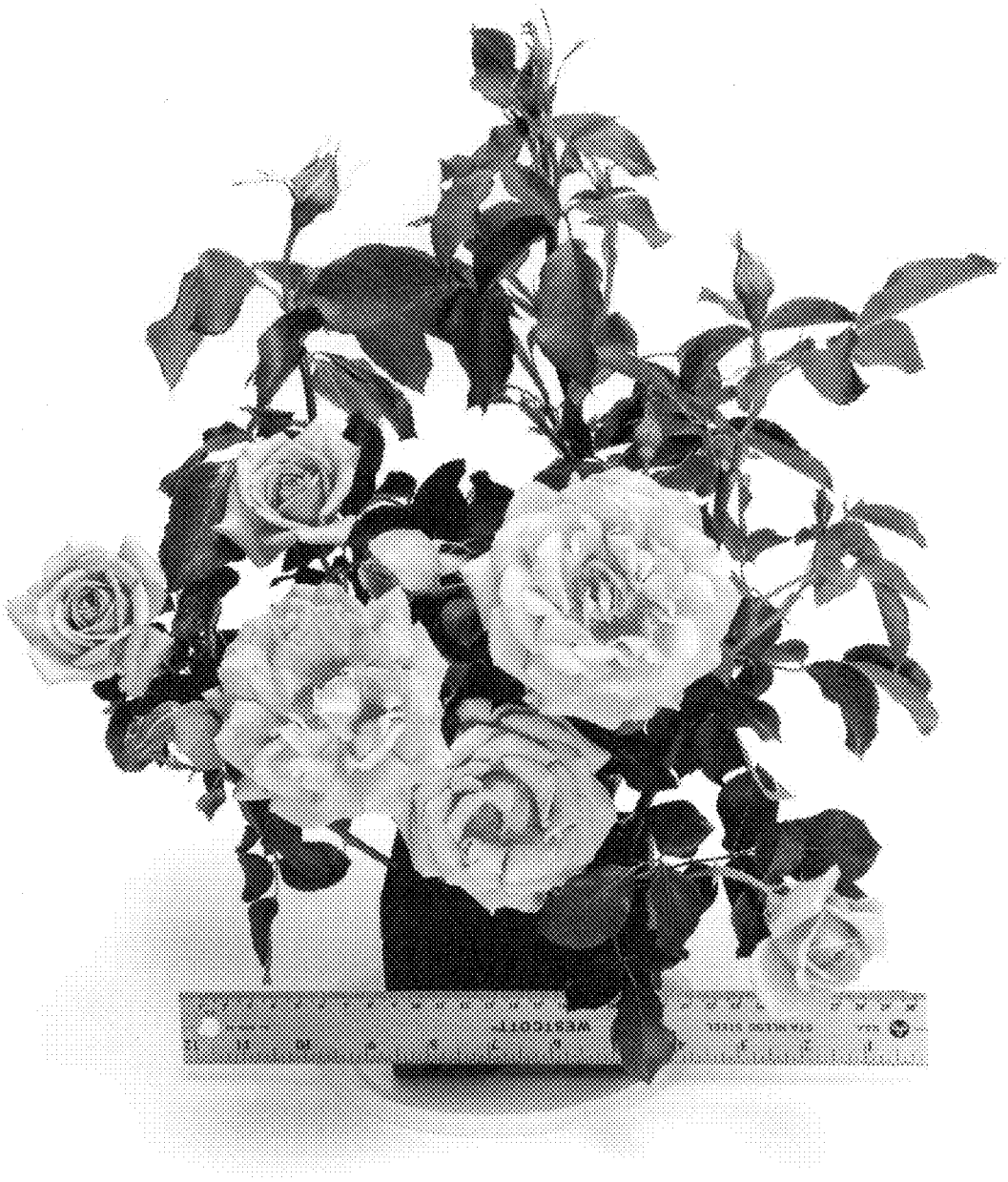

* * * * *